United States Patent [19]

Sanders et al.

[11] Patent Number: 5,291,418
[45] Date of Patent: Mar. 1, 1994

[54] ADJUSTMENT OF ELECTRIC POTENTIAL BY AUTOMATIC TITRATION

[75] Inventors: James M. Sanders, Rochester; Ming-Jye Lin, Penfield; Michael P. Lionti, Rochester; Michael C. Schrader, Honeoye Falls, all of N.Y.

[73] Assignee: Eastman Kodak Company, Rochester, N.Y.

[21] Appl. No.: 731,166

[22] Filed: Jul. 5, 1991

[51] Int. Cl.$^5$ .................................... G06F 15/46
[52] U.S. Cl. ................................. 364/500; 436/51
[58] Field of Search .................. 204/400; 436/51; 364/500

[56] References Cited

U.S. PATENT DOCUMENTS

| | | | |
|---|---|---|---|
| 3,073,682 | 1/1963 | Lindsley | 436/51 |
| 3,506,405 | 4/1970 | Christie et al. | |
| 3,578,408 | 5/1971 | Sirois et al. | 436/51 |
| 3,692,483 | 9/1972 | Sternberg | 436/51 |
| 3,730,685 | 5/1973 | Prohaska | |
| 3,769,178 | 10/1973 | Rothermal, Jr. | |
| 3,870,466 | 3/1975 | Rellstab et al. | |
| 4,007,105 | 2/1977 | Buzza et al. | |
| 4,058,365 | 11/1977 | Krogh | 436/51 |
| 4,227,973 | 10/1980 | Ruzicka et al. | |
| 4,266,942 | 5/1981 | Vandenbossche et al. | |
| 4,302,299 | 11/1981 | Ishikawa | |
| 4,312,715 | 1/1982 | Albery et al. | 436/51 |
| 4,859,608 | 8/1989 | Frueh | |
| 4,912,417 | 3/1990 | Gibboney et al. | 204/400 |
| 4,940,551 | 7/1990 | Riggs et al. | |
| 5,022,980 | 6/1991 | Tanaka et al. | 204/400 |

FOREIGN PATENT DOCUMENTS

0457989A1  11/1991  European Pat. Off.
2740570   3/1978  Fed. Rep. of Germany.

OTHER PUBLICATIONS

Analytical Chemistry, vol. 50, No. 6, May 1978, pp. 718-722 D. J. Legget, *Microcomputer Controlled Potentiometric Titration System for Equilibrium Studies*.

Primary Examiner—Jack B. Harvey
Assistant Examiner—Thomas Peeso
Attorney, Agent, or Firm—Nixon, Hargrave, Devans & Doyle

[57] ABSTRACT

Automatic titration method and apparatus provides for adjustment of the electric potential of a solution. A programmed computer responsive to iterative measurements of the potential regulates a two-phase adjustment process which approaches the desired electric potential (overall aim) using sub-aims thereby preventing overshoot of the overall aim.

22 Claims, 3 Drawing Sheets

ADJUSTMENT OF ELECTRIC POTENTIAL BY AUTOMATIC TITRATION

FIELD OF INVENTION

This invention relates to a system (method and apparatus) for the adjustment of electric potential of a liquid material to a predetermined aim by computercontrolled titration.

BACKGROUND OF THE INVENTION

Titration is generally known as a method of determining volumetrically the concentration of a substance in a subject material by adding a standard solution of known volume and strength (this standard solution is known as the "titrant") to the subject material until a given reaction is completed.

Typically, titration is carried out to the "endpoint", i.e. the point at which the given reaction is complete, to determine the concentration of a given substance in the material. Various potentiometric, colorimetric, and coulometric titration processes are known in the art. Potentiometric determination methods are generally based on the determination of pH, ion activity, redox and other chemical potentials. Uses of titration techniques include determination of the contents of a chemical solution (See, U.S. Pat. No. 4,859,608 to Frueh) or to determine the concentration of certain functional chemical groups in a solution (See, U.S. Pat. No. 3,730,685 to Prohaska).

Titration processes require a high degree of precision, extensive operator interaction and are generally very time corisuining. Further, because the amount of titrant added to a solution to yield a given change will vary dramatically as the electric potential changes, overshooting the endpoint of a titration often occurs. Overshooting the endpoint of a titration results in inaccurate and often useless data or results.

In an effort to increase the accuracy and efficiency of titration processes, automatic titration systems have been developed. Most often these systems take the form of titration-to-endpoint methods mentioned above. In a typical endpoint system, the automatic titrator will produce a recording of the entire titration curve from which the endpoint may be determined.

In the curve-recording type of automatic system, titrant is delivered by means of a motor-driven syringe, or burette, through a capillary whose tip is immersed in a rapidly stirred solution. The motor drive is coupled to the drive mechanism of a recording potentiometer, with the recording chart divisions being directly related to the titrant delivered. The measured potential variations are automatically plotted on the chart, and by inspection of the plotted curve, the entrance and exit of the steep portion of the curve in which an inflection occurs can be located. By taking half the distance between these points, a close estimate of the endpoint is obtained.

One of the key advantages of an automatic titrator is that a large number of similar titrations can be performed in a short period of time, but the requirement for manual determination of the endpoint in each case obviates this advantage. In addition, poor results can occur if there is a slow attainment of equilibrium in the solution during the titration, or if the mixing rate is inadequate. This problem can be overcome to some extent by the use of an "anticipation" technique wherein the rate of titrant addition is automatically slowed as the end point is approached. However, anticipation does not entirely eliminate the problem, for the slower rate itself introduces errors and also reduces the advantage of the automatic system. It should also be noted that in many titrations, the points of inflection (areas of rapid change in electric potential that are indicative of the endpoint) on the plotted curve are very difficult to locate with any accuracy, and this introduces further error in the measurements.

There are many examples of automated titration-to-endpoint processes. U.S. Pat. No. 3,730,685 to Prohaska discloses a computer-controlled process whereby a program is used to analyze the progress of the titration curve by determining the slope of the curve after each incremental addition of titrant. The maximum slope of the curve is calculated to determine the endpoint of the titration.

U.S. Pat. No. 3,769,178 to Rethermal, Jr., discloses an automatic titration process that plots the first derivative of the titration curve in an attempt to more accurately determine the endpoint of the titration.

Other methods of automatic titration to determine the end point of the titration are disclosed in U.S. Pat. No. 4,266,942 to Vandenbossche et al., U.S. Pat. No. 4,302,299 to Ishikawa, and U.S. Pat. No. 4,859,608 to Frueh.

Titration processes may also be used to adjust the electric potential of a subject material. The adjustment may take the form of, for example, pH modification or the modification of the ion concentration in a material. U.S. Pat. No. 4,940,551 to Riggs et al. discloses a process where predetermined dispenses are injected into a fluid stream to create an in-situ titration curve to calculate one total dispense to obtain a desired pH. However, this system is slowed by the fact that the titration curve must be created before adjustment may commence.

The known processes utilizing automatic titration have been unable to completely solve such problems as excessive overshooting of the aim or endpoint, slow titration times or the requirement of operator interaction. Further, the known processes utilizing automatic titration are often restricted to pH applications or are designed for application only in titration-to-endpoint systems.

SUMMARY OF THE INVENTION

The present invention relates to a system (method and apparatus) for computer-controlled adjustment of the electric potential of a given material in liquid form. For the purposes of this invention, the electric potential to be adjusted may be in the form of a pH value, ion concentration (i.e., silver ion concentration measured in millivolts), redox or other chemical potentials. Controlled adjustment in accordance with the invention is to an "aim" which is not necessarily the endpoint but is a predetermined value of electric potential, which may correspond to a pH other than in the vicinity of a neutral pH (e.g. the aim for typical photographic emulsion of interest would be in the range of 4 to 7.5 pH units).

The method of the present invention utilizes a computer program to complete the electric potential adjustment of the material quickly and efficiently. The present process comprises two general phases: (a) a start-up phase, and (b) a final adjustment phase. The start-up phase is designed to calculate initial dispenses of titrant incrementally. The first initial dispense is calculated based on the slope number of other, previous titration curves of similar material.

The start-up phase is designed to use redispenses that are multiples of the first initial dispense until the electric potential is adjusted a desired minimum number of units toward the overall aim. This provides a minimum initial adjustment of the potential. After the minimum initial adjustment is made, the process proceeds to the final adjustment phase. Dispenses in the final adjustment phase may be calculated in one of two ways. If there were at least two dispenses during the start-up phase of the process, the next dispense will be calculated by fitting the data points to a mathematical equation and thereby extrapolating the volume of the next dispense. For example, the dispense may be calculated by application of a quadratic equation in which the measured electric potential is the principal parameter. However, if a mathematical expression cannot be established to fit through the data points that represent the previous dispenses (i.e., a positive real root of the quadratic expression for the fit not determined) then linear extrapolation must be used.

Therefore, if there has only been one dispense during the start-up phase, or there has been more than one dispense during the start-up phase but a mathematical expression cannot be fit relative to the data points, the dispense will be calculated by linear extrapolation.

In either case, the final adjustment phase of the process relies on the construction of a moving, in-situ titration curve that essentially plots the electric potential versus titrant volume and estimates future dispenses based on this curve.

To address the problem of overshoot, a sub-aim strategy is implemented in the final adjustment phase. The adjustments are made relative to these sub-aims, which approach the aim value. Additionally, the process is designed to terminate if certain events occur that decrease the accuracy of the adjustment.

The present invention also relates to computer aided apparatus for adjusting electric potential that carries out of the above-described method.

The principal object of the present invention is to provide a system (method and apparatus) of computer-controlled adjustment of the electric potential of a quantity of material that is quick, efficient, exhibits a very small amount of aim overshoot and requires minimal operator interaction, which system is versatile and may be utilized to titrate materials of differing sensitivities to changes in titrant that may be known or unknown.

DETAILED DESCRIPTION OF THE INVENTION

Figure 1:
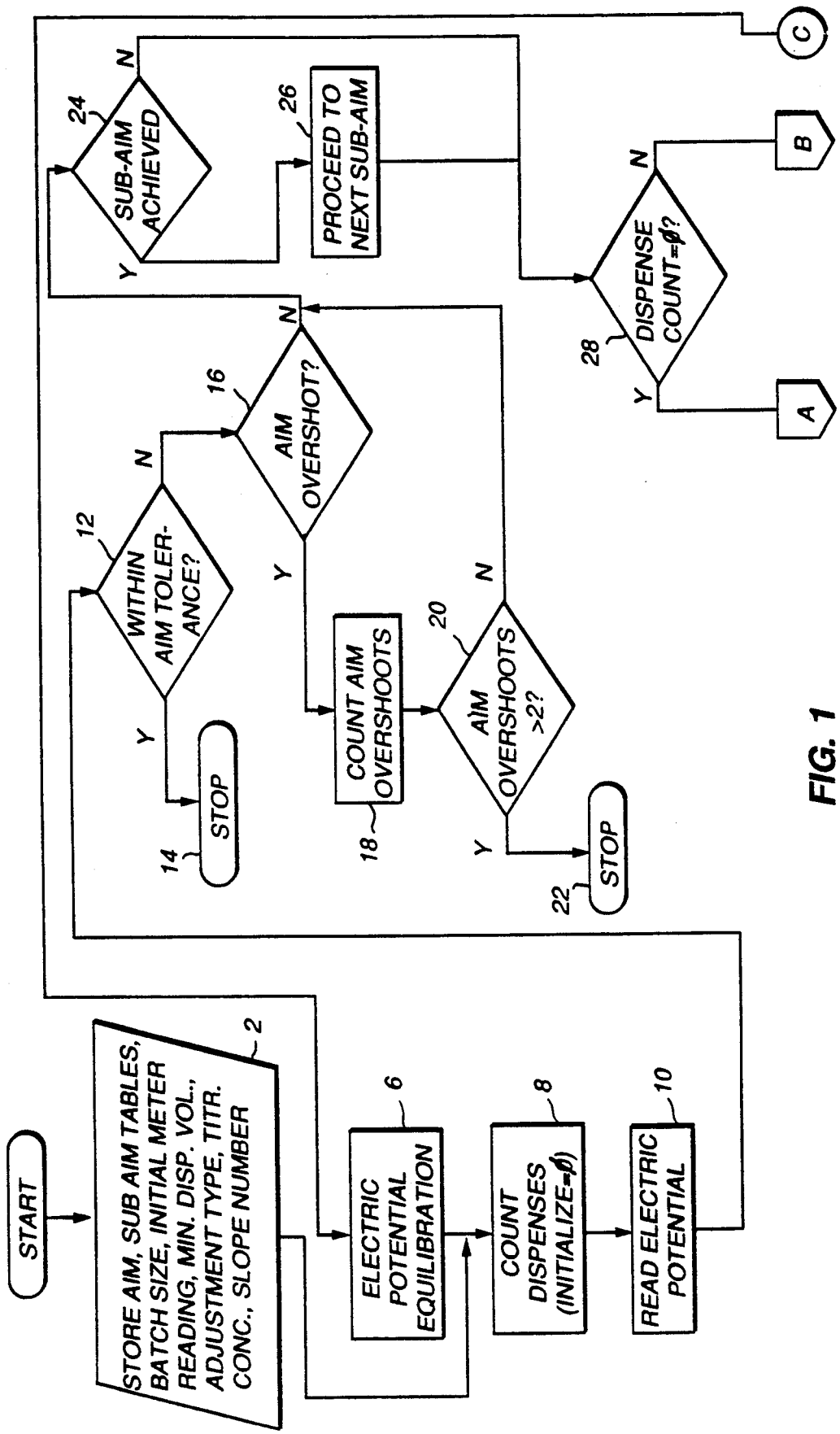
FIG. 1 and FIG. 1 (cont.) constitute a flow chart depicting the program of the electric potential adjustment system of the present invention.
Figure 1:
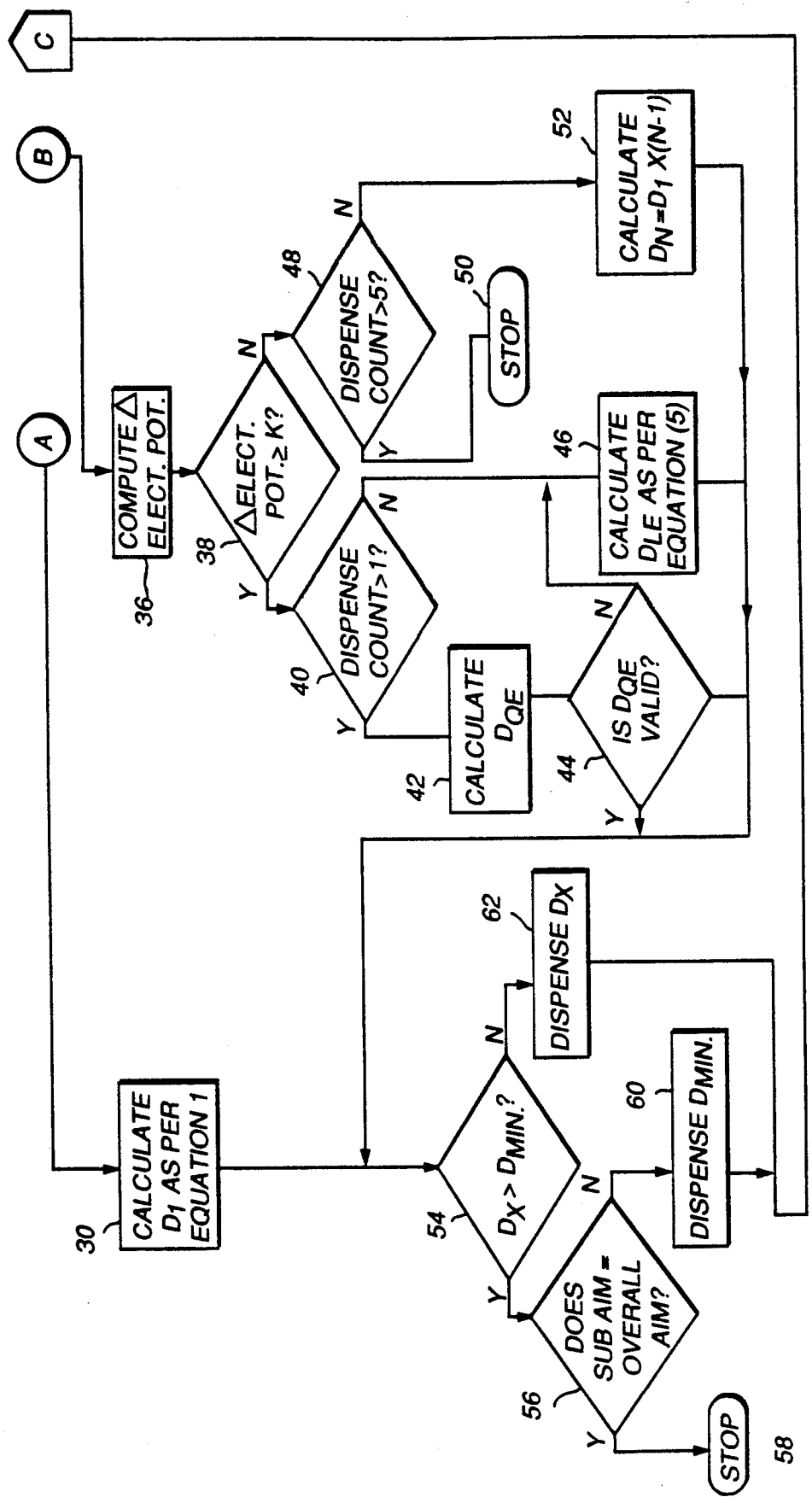
Figure 2:
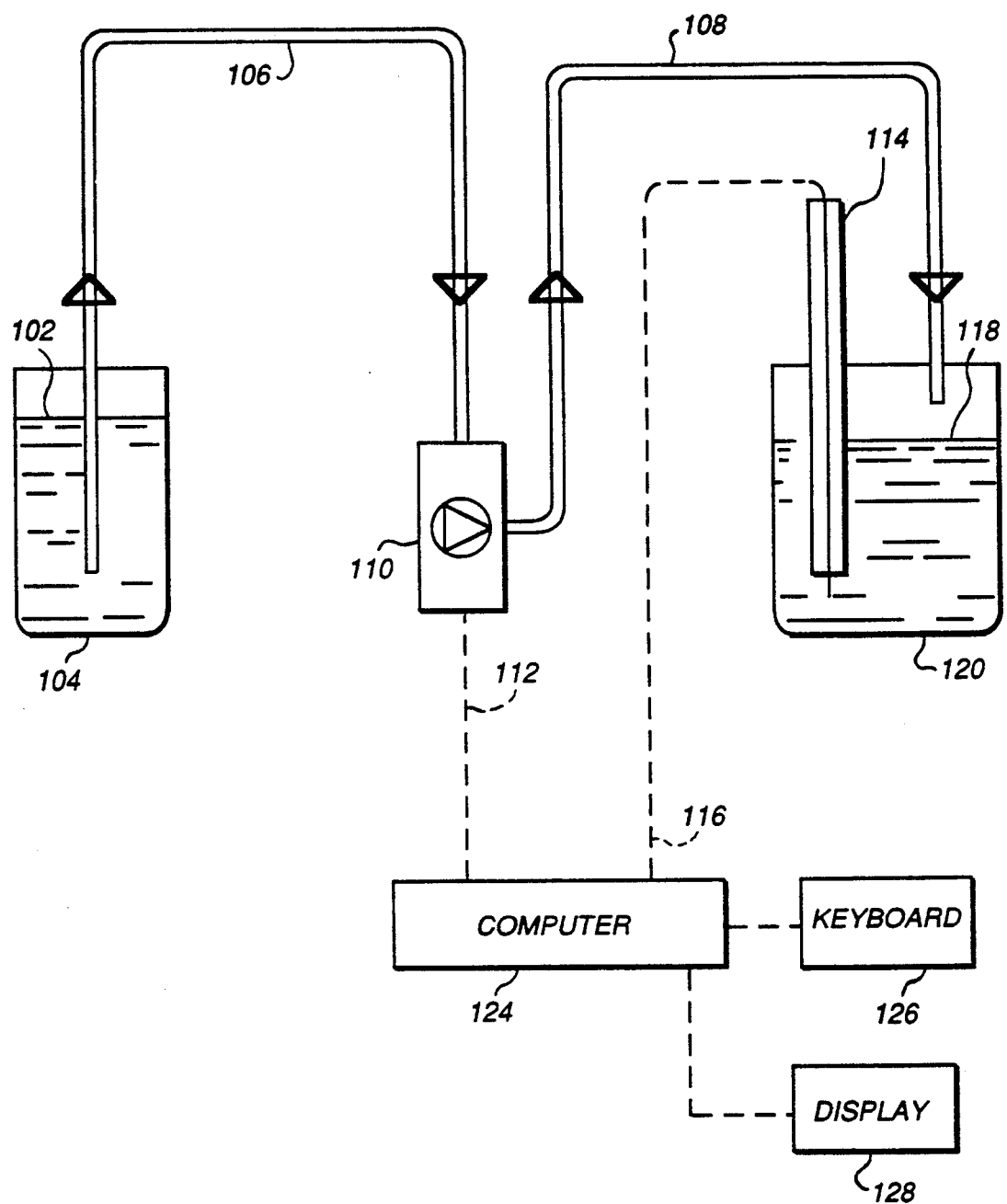
FIG. 2 is a diagrammatic illustration of one embodiment of an automatic titration system in accordance with the present invention.

Referring to FIG. 2, shown is a diagrammatic illustration of one embodiment of an automatic titration system in accordance with present invention. The system of the present invention has wide-scale applicability to a variety of areas where adjustment by a method of potentiometric titration is useful such as pH adjustment, ion concentration adjustment or redox reaction processes. The present process has shown particular utility in the adjustment of pH and/or silver ion concentration of silver halide based photographic emulsions that are known in the art.

As shown in FIG. 2, titrant 102 is supplied from storage receptacle 104 (i.e., a beaker) by an automatic dispenser 110 which is commanded to produce dispenses (incremental volumes of the titrant) by an electrical compound signal which is outputted from a control computer 124 on electrical output line 112. Titrant 102 is pumped by a pump in dispenser 110 that is activated by the computer output.

Conduits 106 and 108 are tubes which carry the titrant. Fluid lines are shown solid and electrical lines are shown broken in FIG. 2. Receptacle 120 contains material 118 of which the electric potential is to be adjusted. The change in the electric potential is sensed by measurement probe 114 which is in contact with material 118 in receptacle 120. Measurement probe 114 is connected via line 116 to control computer 124 which digitizes the probe signal and contains the program which carries out the automatic titration method of the present invention.

Computer 124 may optionally include keyboard 126 for inputting data or other parameters, or a display 128 which may be a printer used to read out the titration results.

The program for the computer is shown for the exemplary case where adjustment of the electric potential of a photographic emulsion is of interest. Upon start, the program proceeds to store certain input parameters as shown at 2. These parameters include the initial meter reading, overall adjustment aim, batch size, titrant concentrations, minimum possible dispense volume and adjustment type (i.e., pH or silver ion concentration), the slope number and the titrant concentration (normality). Keyboard 126 may be used to input these parameters or they may be passed from other software programs integrated into computer 124.

As described above, the process of the present invention comprises two general phases: a start-up phase and a final adjustment phase. Additionally, the program has a system which tracks each dispense that is computed in the start-up and final adjustment phases. This system consists of the operations shown at 8 through 28.

The total number of dispenses during both the start-up and final adjustment phases is counted by operation 8. The electric potential is read as shown by operation 10. In this preferred embodiment, the electric potential is in the form of a pH or a value (in millivolts) representing the silver ion concentration of the material.

Next, decision 12 determines whether or not the reading is within the "aim tolerance". For purposes of this invention, the aim tolerance of an adjustment is the acceptable range of values on either side of the aim. The aim tolerance is an input which is stored upon initialization and may be set dependent on the needs and requirements of the individual adjustment being made. When the reading falls within the aim tolerance, the adjustment is stopped as indicated by terminal 14.

If the reading is not within aim tolerance, a decision 16 is made as to whether the aim has been overshot. If the aim has been overshot, the number of overshoots are counted by counting operation 18. If there have been more than two aim overshoots decision 20 recognizes that event and the adjustment procedure is stopped as indicated by terminal 22.

An integral part of the process of the present invention is the use of a sub-aim strategy. This enables the adjustments to be made rapidly without overshooting the desired aim value by using a series of sub-aims which approach the final aim value. This minimizes the chance of overshoots while maintaining aggressive movement toward the final adjusted aim.

Sub-aims may be determined in a variety of ways. In a preferred embodiment of the present process the sub-aims are determined from step tables. The step tables have two parts, one part is a sequence of steps (sub-aims) for approaching the overall aim and the other part is the range "in front of" each step to determine when the meter reading has been brought close enough to that step for the program to shoot for the next step. An exemplary pH step table used in a preferred embodiment of the process of the present invention is represented by Table I.

TABLE I

| If the reading is greater than the amount set forth in col. I from aim ...<br>I<br>(pH units) | But not more than the amount set forth in col. II from aim ...<br>II<br>(pH units) | Then the sub-aim is the difference between the overall aim and the amount set forth in col. III from aim<br>III<br>(pH units) |
|---|---|---|
| 2.90 | no limit | 2.80 |
| 2.08 | 2.90 | 2.00 |
| 1.56 | 2.08 | 1.50 |
| 0.89 | 1.56 | 0.85 |
| 0.43 | 0.89 | 0.40 |
| 0.24 | 0.43 | 0.22 |
| 0.13 | 0.24 | 0.12 |
| 0.07 | 0.13 | 0.06 |
| 0.00 | 0.07 | 0.00 |

In another embodiment of the present process, the sub-aims may be set to change the electric potential by half the change needed to reach the aim (i.e. one-half the difference between the initial meter reading and the overall aim). The next sub-aim would be the overall aim value. This sub-aim method is used to approach the aim more aggressively when the possibility of overshoot is minimal, i.e. for adjustments where the slope of the titration curve is continuously decreasing. Additionally, a sub-aim may be established whereby the first sub-aim is the overall aim if the initial electric potential reading is within a predetermined number of units (pH units or millivolts) of the final aim.

The sub-aims are accessed, one at a time, in operations 24 and 26.

After the program has looped through the tracking operations, the program branches as determined by decision 28 based upon the dispense count. When the count equals zero the start-up phase is entered. The dispenses calculated and made during the start-up phase ("initial dispenses") are calculated according to a predetermined start-up strategy. The start-up strategy may take any number of forms depending on the nature of the adjustment being made (i.e. pH or ion concentration), the data available, or the nature of the material being adjusted. The start-up strategy should be designed to make some minimal adjustment in the material before enough data has been obtained to use the more accurate methods of calculating dispense volumes that are embodied in the final adjustment phase. Additionally, the start-up strategy is designed to facilitate quick approach to the aim while minimizing the possibility of overshoot.

Exemplary start-up strategies may include a predictive component where equations are established that take into account certain parameters of the material being adjusted. These equations may be used to calculate initial dispenses that will give a desired initial adjustment. Another exemplary start-up strategy might involve the use of an initial bulk dispense of titrant to adjust the material by a relatively larger amount and calculate initial dispenses based upon the material's response to the bulk addition.

A particularly preferred start-up strategy when adjusting silver halide based photographic emulsions is to calculate initial dispenses of titrant based on the slope number of a historical titration curve over a region of adjustment of the electric potential. The slope number represents an estimate of a titration curve slope over a region of adjustment of the material being adjusted. The titration curve from which the slope number is derived is based on batch history data from previous adjustments made on the same or similar material. The slope number quantifies the amount of titrant needed per unit change (i.e., pH units or millivolts) per unit mass of batch. The dispense volume is calculated at operation 30 using the slope number according to the following equation, denominated as Equation 1:

$$\text{Order} = (\text{slope})\,[\text{ABS}(\gamma_{pred} - \text{Reading})] \quad (1)$$
$$(\text{Mass})\,[(\text{SlopeCon})/(\text{TitrCon})]\,(\text{ESF})$$

wherein
Order = dispense volume (milliliters)
Slope = slope number (milliliters/unit of electric potential/kg batch)
ABS = absolute value function
$\gamma$pred = sub-aim for dispense
Reading = meter reading
Mass = batch mass (kilograms)
TitrCon = actual titrant concentration (normality)
ESF = extrapolation safety factor
SlopeCon = concentration of titrant used to define the slope number The extrapolation safety factor ("ESF") is implemented to prevent overshoots. This factor may be adjusted to cause the program to recommend some percentage of the full dispense calculated. The amount of the factor will vary depending on the type and nature of the adjustment. In this preferred embodiment, an ESF of 0.25 has been found particularly useful.

In a typical automatic titration system, dispenser 110 is capable of dispensing a minimum volume or more of titrant depending upon the command from computer 124 (FIG. 2). Therefore, after the initial dispense has been calculated in operation 30, the program compares the computed dispense volume with the minimum dispense volume (the minimum being stored upon initialization at operation 2) and decision 54 determines whether or not the dispense calculated is less than the minimum dispense volume of dispenser 110. If the initial dispense is below the minimum dispense, the sub-aim in effect is compared with the final aim at operation 56 to determine if the sub-aim for the adjustment equals the overall aim. If the sub-aim does not equal final aim the minimum volume (Dmin) is dispensed. If the sub-aim equals the overall aim, the process stops as shown at 58. If the calculated initial dispense ($D_x$) is not less than the minimum dispense (Dmin), the calculated initial dispense Dx is made as shown at 62.

At this point, the program provides time for equilibration of the electric potential as shown at 6. The program then returns to step 8 and the dispenses are counted. The electric potential is read at step 10. Decisions 12 and 16 are applied to determine if the electric potential is within aim tolerance or if the aim has been overshot. Next step 24 is carried out. There it is determined if the sub-aim has been achieved. If the sub-aim is achieved, the program will jump to the next sub-aim as shown at operation 26.

If decision 28 determines the dispense count does not equal zero then the total change in the electric potential ($\Delta$) is computed at operation 36. If decision 38 determines that the original electric potential has been changed by less than a predetermined number of units, then the process will remain in the start-up phase for up to four more dispenses as shown at 48 (or until the minimum adjustment is attained). This continuation of the start-up phase provides flexibility when something has gone wrong with the adjustment (i.e., subject material buffered heavily, titrant or subject material concentrations erroneously determined, etc.)

The next dispenses ("redispenses") in the start-up phase ("$D_N$") are multiples of the initial dispense. Up to four redispenses of volume $D_N$ are computed in operation 52 based upon the initial dispense volume. The first redispense will be the same volume as the initial dispense. The second redispense will be two times the initial dispense. The third redispense will be three times the initial dispense and the fourth redispense will be four times the initial dispense. If the electric potential has not been adjusted the minimum amount after five dispenses as shown at 48, the adjustment will cease and the program terminates as shown at 50.

If the electric potential has been adjusted the minimum amount (K, as determined at decision 38), the start-up phase of the adjustment is complete. The program then proceeds into the final adjustment phase. In the final adjustment phase, the preferred method relies on the construction of a moving, in-situ titration curve that essentially plots the electric potential versus titrant volume for the last three data points and estimates future dispenses based on this curve. If less than three points of collected data exist, the curve will be based on whatever data has been compiled to that point.

Decision 40 determines if the dispense count is greater than one. If the dispense count is not greater than one, the first final dispense must be computed using a linear extrapolation of the response from the first initial dispense. The linear extrapolation is computed in operation 46 according to the following equation:

$$\text{Order} = (\text{PrvOrd})\,[(\gamma_{pred} - \text{Reading})/(\text{Reading} - \text{OldRdg})]\,(\text{Alpha}) \quad (2)$$

wherein
Order = dispense volume (milliliters) = $D_{LE}$
PrvOrd = previous dispense (milliliters)
$\gamma$pred = sub-aim for dispense
Reading = meter reading
OldRdg = previous meter reading
Alpha = linear extrapolation coefficient The linear extrapolation coefficient ("alpha") represents the fraction of the full dispense amount calculated by the linear extrapolation. Alpha is similar to the extrapolation safety factor discussed above. Alpha is a variable implemented to minimize the possibility of overshoots and may be dependent on a number of factors. In the embodiment presently described, for example, the type, range and direction of the adjustment were used to set alpha values. In general, it has been found that a higher alpha value may be used where the slope of the titration curve over the region of adjustment is decreasing because in that situation the chance of overshoot is less.

The calculated dispense $D_{LE}$ is treated as $D_x$ as the program loops through operations 54, 56, 58, 60 and 62 and continues to loop through the control operations 12-28 and back, via connectors B—B, to compute the potential change $\Delta$ which determines whether further dispenses in the final adjustment phase are required.

If decision 40 determines that the dispense count is greater than one the program will attempt to extrapolate the next dispense volume by using a curve-fitting mathematical equation. The type of mathematical equation used is dependent on the type of adjustment and data obtained. For example, any number of polynomial equations, equations implementing natural logarithmic functions or equations implementing trigonometric functions may be used. In this embodiment of the method of the present invention, it has been found that extrapolation from a quadratic equation is particularly useful. In the present process, it is preferred to fit the quadratic through the last three data points and base the next dispense upon this curve. The quadratic extrapolation is carried out in operation 42 according to the following equation:

$$\emptyset = (0.5)\,(\ddot{\gamma}_{curr})\,(\text{delta})^2 + (\dot{\gamma}_{curr})\,(\text{delta}) + (\gamma_{curr} - \gamma_{pred}) \quad (3)$$

wherein
$\emptyset$ = zero
delta = dispense volume (milliliters) = $D_{QE}$
$\ddot{\gamma}$curr = second derivative of meter reading with respect to titrant volume
$\dot{\gamma}$curr = first derivative of meter reading with respect to titrant volume
$\gamma$curr = current meter reading
$\gamma$pred = sub-aim for dispense
This equation will result in a positive real root if the extrapolation is valid.

Next, test 44 will determine if the quadratic extrapolation has been successful and whether $D_{QE}$ is valid. If a positive real root is found, the quadratic extrapolation is successful and $D_{QE}$ is taken as valid and used as $D_x$ in the same loop as used for $D_{LE}$ as discussed above. If a positive real root is not found then the next dispense is calculated by the linear extrapolation operation as shown at 46.

As with the start-up phase of the adjustment, all dispenses in the final adjustment phase go through decision 54 to determine if the calculated dispense is less than the minimum dispense volume of the dispensing means. If the dispense is less than the minimum dispense and the aim does not equal the overall sub-aim, the minimum volume is dispensed at 60. Otherwise, the volume calculated by either the quadratic extrapolation or the linear extrapolation is dispensed at 62.

Once the process is in the final adjustment phase, all remaining final dispenses are calculated utilizing the curve-fitting mathematical equation (i.e. quadratic extrapolation) if possible, in accordance with the above-described process, relative to the accessed sub-aims. The program will proceed from sub-aim to sub-aim until the electric potential has been adjusted to the predetermined, final aim.

Although the invention has been described in detail for the purpose of illustration, it is understood that such detail is for that purpose and variations can be made therein by those skilled in the art without departing from the spirit and scope of the invention. The foregoing description should therefore be taken as illustrative and not in a limiting sense.

What is claimed is:

1. A titration control process for adjusting an electric potential of a material to a predetermined final aim, said process comprising the following steps:
   a. measuring the original electric potential of said material;
   b. calculating, in accordance with a predetermined start-up strategy, an amount of titrant to be added to said material as a calculated initial dispense and adding said calculated initial dispense to said material;
   c. calculating an amount of titrant to be added as a redispense of titrant to said material and, in accordance with said calculating, redispensing said titrant to said material based on (1) said calculating initial dispense of titrant to said material and (2) the electric potential of said subject material upon each redispense until said electric potential is adjusted a minimum amount;
   d. making final dispenses of said titrant to said material by adding a fixed, incremental quantity of titrant of said material, wherein said fixed, incremental quantity is based upon (1) either a linear extrapolation relative to the last two data points or an extrapolation based on a mathematical expression relative to three or more data points, relative to a series of sub-aims which correspond to potentials approaching said predetermined final aim and (2) measurements of said electric potential upon each said final dispense until said electric potential is adjusted to said predetermined final aim.

2. The process according to claim 1, wherein said predetermined start-up strategy is using the slope number of a historical titration curve over a region of adjustment of said electric potential.

3. The process according to claim 2, wherein said calculation of said calculated initial dispense is carried out using said slope number according to the following equation:

$$\text{Order} = (\text{slope})(\text{ABS}(\gamma_{pred} - \text{Reading}))(\text{Mass})\left(\frac{(\text{SlopeCon})}{(\text{TitrCon})}\right)(\text{ESF})$$

wherein:
Order = dispense volume (milliliters)
Slope = slope number (milliliters/unit of electric potential/kg batch)
ABS = absolute value function
$\gamma$pred = sub-aim for dispense
Reading = meter reading
Mass = batch mass (kilograms)
TitrCon = titrant concentration (normality)
ESF = extrapolation safety factor
SlopeCon = concentration of titrant used to define the slope number.

4. The process according to claim 2, wherein said calculation of said calculated initial dispense is carried out using said slope number according to the following equation:

$$\text{Order} = (\text{PrvOrd})\left(\frac{(\gamma_{pred} - \text{Reading})}{(\text{Reading} - \text{OldRdg})}\right)(\text{Alpha})$$

wherein:
Order = dispense volume (milliliters)
PrvOrd = previous dispense (milliliters)
$\gamma$pred = sub-aim for dispense
Reading = meter reading
OldRdg = previous meter reading
Alpha = linear extrapolation coefficient.

5. The process according to claim 1, wherein said extrapolation is a quadratic extrapolation and said mathematical expression is a quadratic equation.

6. The process according to claim 5, wherein said quadratic extrapolation is carried out according to the following equation relative to the last three said data points:

$$\emptyset = (0.5)(\ddot{\gamma}_{curr})(\text{delta})^2 + (\dot{\gamma}_{curr})(\text{delta}) + (\gamma_{curr} - \gamma_{pred})$$

wherein
$\emptyset$ = zero
delta = dispense volume (milliliters)
$\ddot{\gamma}$curr = second derivative of meter reading with respect to titrant volume
$\dot{\gamma}$curr = first derivative of meter reading with respect to titrant volume
$\gamma$curr = current meter reading
$\gamma$pred = sub-aim for dispense.

7. The process according to claim 1, wherein said series of sub-aims vary in steps and are all less than or equal to said predetermined final aim in value.

8. The process according to claim 1, wherein said series of sub-aims are set to change said electric potential by half of the change needed to reach the final aim value.

9. The process according to claim 1, wherein said material is a silver halide based photographic emulsion.

10. The process according to claim 1, wherein said electric potential represents the pH of said material.

11. The process according to claim 1, wherein said electric potential represents an ion concentration of said material.

12. A titration control apparatus for adjusting an electric potential of a material to a predetermined final aim, said apparatus comprising:
   a. means for measuring the original electric potential of said material;
   b. means for calculating, in accordance with a predetermined start-up strategy, an amount of titrant to be added to said material as a calculated initial dispense and adding said calculated initial dispense to said material;
   c. means for calculating an amount of titrant to be added as a redispense of titrant to said material and, in accordance with said calculating, redispensing said titrant to said material based on (1) said calculated initial dispense of titrant to said material and (2) the electric potential of said material upon each redispense until said electric potential is adjusted a minimum amount;

d. means for making final dispenses of said titrant to said material by adding a fixed, incremental quantity of titrant to said material, wherein said fixed, incremental quantity is based upon (1) either a linear extrapolation relative to the last two data points or an extrapolation based on a mathematical expression relative to three or more data points, relative to a series of sub-aims which correspond to potentials approaching said predetermined final aim and (2) measurements of said electric potential of said material upon each said final dispense until said electric potential is adjusted to said predetermined final aim.

13. The apparatus according to claim 12, wherein said means for calculating said initial dispense calculates said initial dispense using a slope number from a historical titration curve over a region of adjustment of said electric potential.

14. The apparatus according to claim 13, wherein said means for calculation of said initial dispense calculates said initial dispense using said slope number according to the following equation:

$$\text{Order} = (\text{slope})(\text{ABS}(\gamma_{pred} - \text{Reading}))(\text{Mass})\left(\frac{(\text{SlopeCon})}{(\text{TitrCon})}\right)(\text{ESF})$$

wherein:
Order = dispense volume (milliliters)
Slope = slope number (milliliters/unit of electric potential/kg batch)
ABS = absolute value function
$\gamma_{pred}$ = sub-aim for dispense
Reading = meter reading
Mass = batch mass (kilograms)
TitrCon = titrant concentration (normality)
ESF = extrapolation safety factor
SlopeCon = concentration of titrant used to define the slope number.

15. The apparatus according to claim 12, wherein said calculation of said means for making said final dispenses calculates said final dispenses based upon said linear extrapolation according to the following equation:

$$\text{Order} = (\text{PrvOrd})\left(\frac{(\gamma_{pred} - \text{Reading})}{(\text{Reading} - \text{OldRdg})}\right)(\text{Alpha})$$

wherein:
Order = dispense volume (milliliters)
PrvOrd = previous dispense (milliliters)
$\gamma_{pred}$ = sub-aim for dispense
Reading = meter reading
OldRdg = previous meter reading
Alpha = linear extrapolation coefficient 16. The apparatus according to claim 12, wherein said extrapolation is a quadratic extrapolation and said mathematical expression is a quadratic equation.

17. The apparatus according to claim 16, wherein said extrapolation based on said quadratic equation is carried out according to the following equation relative to the last three said data points:

$$\emptyset = (0.5)(\ddot{\gamma}_{curr})(\text{delta})^2 + (\dot{\gamma}_{curr})(\text{delta}) + (\gamma_{curr} - \gamma_{pred})$$

wherein
$\emptyset$ = zero
delta = dispense volume (milliliters)
$\ddot{\gamma}_{curr}$ = second derivative of meter reading with respect to titrant volume
$\dot{\gamma}_{curr}$ = first derivative of meter reading with respect to titrant volume
$\gamma_{curr}$ = current meter reading
$\gamma_{pred}$ = sub-aim for dispense 18. The apparatus according to claim 12, wherein said series of sub-aims vary in steps that approach said final aim value.

19. The apparatus according to claim 12, wherein said series of sub-aims are set to change said electric potential by half of the change needed to reach the final aim value.

20. The apparatus according to claim 12, wherein said material is a silver halide based photographic emulsion.

21. The apparatus according to claim 12, wherein said electric potential represents the pH of said subject material.

22. The apparatus according to claim 12, wherein said electric potential represents an ion concentration of said material.

* * * * *